(12) United States Patent
Tekavec et al.

(10) Patent No.: US 8,697,615 B2
(45) Date of Patent: Apr. 15, 2014

(54) POLYEPIHALOHYDRIN REVERSE EMULSION BREAKERS

(75) Inventors: Thomas N. Tekavec, Houston, TX (US); Marcus D. Faust, Jr., Houston, TX (US)

(73) Assignee: Nalco Company, Naperville, IL (US)

( * ) Notice: Subject to any disclaimer, the term of this patent is extended or adjusted under 35 U.S.C. 154(b) by 39 days.

(21) Appl. No.: 12/967,811

(22) Filed: Dec. 14, 2010

(65) Prior Publication Data

US 2012/0149609 A1   Jun. 14, 2012

(51) Int. Cl.
C09K 8/88 (2006.01)

(52) U.S. Cl.
USPC ........... 507/261; 507/266; 507/921; 507/922; 166/305.1

(58) Field of Classification Search
CPC .......... C09K 8/885; C09K 8/605; C09K 8/88; C09K 2208/12
USPC ............... 507/261, 266, 921, 922; 166/305.1, 166/380.1; 516/191
See application file for complete search history.

(56) References Cited

U.S. PATENT DOCUMENTS

| | | | |
|---|---|---|---|
| 2,470,829 A | 5/1949 | Monson | |
| 2,944,978 A | 10/1960 | Monson | |
| 3,576,740 A | 4/1971 | Annand | |
| 3,591,520 A * | 7/1971 | McDonald | 516/142 |
| 3,746,678 A | 7/1973 | Dick | |
| 3,864,288 A | 2/1975 | Riew et al. | |
| 3,929,635 A | 12/1975 | Buriks et al. | |
| 4,374,734 A | 2/1983 | Newcombe | |
| 4,384,977 A * | 5/1983 | Duke | 516/163 |
| 4,444,654 A | 4/1984 | Cargle et al. | |
| 4,828,726 A | 5/1989 | Himes et al. | |
| 5,032,085 A | 7/1991 | Alwine et al. | |
| 5,152,927 A | 10/1992 | Rivers | |
| 5,247,087 A | 9/1993 | Rivers | |
| 5,643,460 A | 7/1997 | Marble et al. | |
| 5,667,727 A | 9/1997 | Breen | |
| 6,172,123 B1 | 1/2001 | Lindert | |
| 2006/0062753 A1 * | 3/2006 | Naraghi et al. | 424/78.27 |
| 2008/0078545 A1 * | 4/2008 | Welton et al. | 166/278 |
| 2009/0065209 A1 * | 3/2009 | Huang et al. | 166/281 |
| 2011/0315604 A1 * | 12/2011 | Nguyen | 208/188 |

OTHER PUBLICATIONS

Z. Ruiquan et al., "Characterization and demulsification of produced liquid from weak base ASP flooding," Colloids and Surfaces, vol. 290, pp. 164-171, (2006).

* cited by examiner

Primary Examiner — Alicia Bland
(74) Attorney, Agent, or Firm — Edward O. Yonter

(57) ABSTRACT

A composition and method for resolving reverse emulsions and complex water external emulsions using one or more polyepihalohydrins, one or more polyelectrolytes thereof, and any combination thereof is disclosed and claimed. The disclosed invention may be used in any crude oil production process where such emulsions are encountered.

16 Claims, 4 Drawing Sheets

POLYEPIHALOHYDRIN REVERSE EMULSION BREAKERS

FIELD OF THE INVENTION

This invention relates generally to emulsion breaker compositions and methods for resolving emulsions of water and oil. More particularly, the invention relates to structurally modified polyepihalohydrins for resolving emulsions of water and oil. This invention has particular relevance to branched and linear polyepihalohydrins and its polyelectrolytes for resolving oil-in-water emulsions and complex water external emulsions.

BACKGROUND OF THE INVENTION

Crude oil produced from geological formations contains various amounts of water. Water and crude oil are naturally non-miscible. When naturally occurring interfacial active compounds are present, however, these compounds can aggregate on the water and oil interface and cause oil droplets to disperse in the water phase. Such water external, oil internal two phase systems are commonly referred as reverse crude oil emulsions and can be quite stable. During crude oil lifting through production tubes, the water and oil encounters an increased mixing energy from rapid flow through chokes and bends. This additional mixing energy can further emulsify the water and oil. The presence of crude oil in water can interfere with water treatment and/or water re-injection systems. In particular, oil-free water is required for applications where water is discharged into the environment, such as overboard water on offshore platforms, or is used in steam generation, such as steam assisted gravity drainage.

Commonly used reverse emulsion-breaking chemicals, or water clarifiers, include the following: tridithiocarbamic acids (U.S. Pat. No. 5,152,927); dithiocarbamic salts (U.S. Pat. No. 5,247,087); dimethylaminoethyl acrylate methyl chloride and/or benzyl chloride quaternary salts (U.S. Pat. No. 5,643,460); polymeric quaternary ammonium betaines (U.S. Pat. No. 3,929,635); and metal salts (zinc chloride, aluminum chloride). Polymeric quaternary ammonium salts and copolymers of acrylic acid and acrylamide have also been used. These compounds, however, may not provide satisfactory performance in all instances. In particular, in extremely cold weather (e.g., −40° C. and below) various problems are known. These active ingredients are typically viscous and require a suitable solvent to reduce the viscosity of the reverse emulsion breaker blend.

A main challenge in oilfield production is the resolution of oil-in-water emulsions, otherwise known as reverse emulsions. Many reverse emulsion breakers also have a small window of treatment dosages, which makes it challenging and difficult to properly control resolution. Complex or multiple emulsions typically require both a reverse and a standard emulsion breaker to aid in its resolution into clean water and dry oil. These two products traditionally are incompatible, so each is typically injected separately.

There thus exists an ongoing need for new, economical and effective chemicals and processes for resolving reverse emulsions and complex emulsions into the component parts of water and oil.

BRIEF SUMMARY OF THE INVENTION

This invention accordingly provides a reverse emulsion breaker composition for resolving water external emulsions of water and oil. In an aspect, the composition comprises an effective amount of one or more polyepihalohydrins. In another aspect, one or more of the polyepihalohydrins is a polyelectrolyte. In a method of resolving a reverse emulsion or complex water external emulsion of water and oil, the invention comprises adding an effective amount of one or more polyepihalohydrins, polyelectrolytes thereof, and any combination thereof.

It is an advantage of the invention to provide a novel demulsifier for resolving oil-in-water emulsions related to petroleum applications.

It is a further advantage of the invention to provide novel demulsifiers that have superior performance and are much more cost effective than those currently known in the art.

It is yet another advantage of the invention to provide a novel demulsifier for resolving oil-in-water emulsions caused by surfactant injection related to enhanced oil recovery.

A further advantage of the invention is to provide a manufacturing advantage of easier temperature control due to a greater mass of material to absorb the heat generated from the reaction thus increasing safety.

An additional advantage of the invention is to provide a manufacturing advantage that allows for the use of less epihalohydrin per batch due to a higher molecular weight glycerol initiator.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION OF THE INVENTION

The term "reverse emulsion breaker" as used herein refers to a class of chemicals used to aid the separation of emulsions (including, simple emulsion of oil-in-water, and multiple/complex emulsions such as water-in-oil-in-water). Chemicals used to treat oil-in-water emulsions are also commonly referred to as water clarifiers. They are commonly used in the processing of crude oil, which is typically produced along with significant quantities of water. In many instances the crude oil may be dispersed or emulsified in the water phase and must be removed from the water prior to the re-injection, processing, or discharge of the water.

Figure 1:
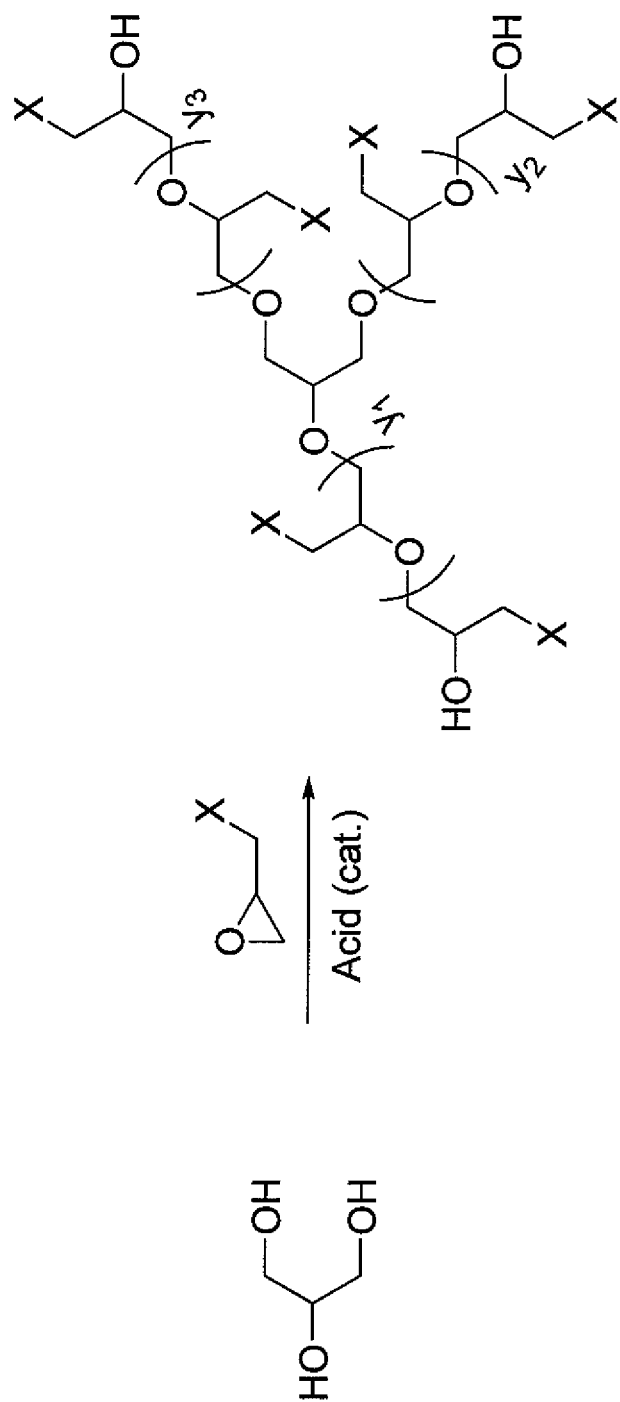
FIG. 1 illustrates the general structure of the polyepihalohydrin compounds of the invention.
Figure 2:
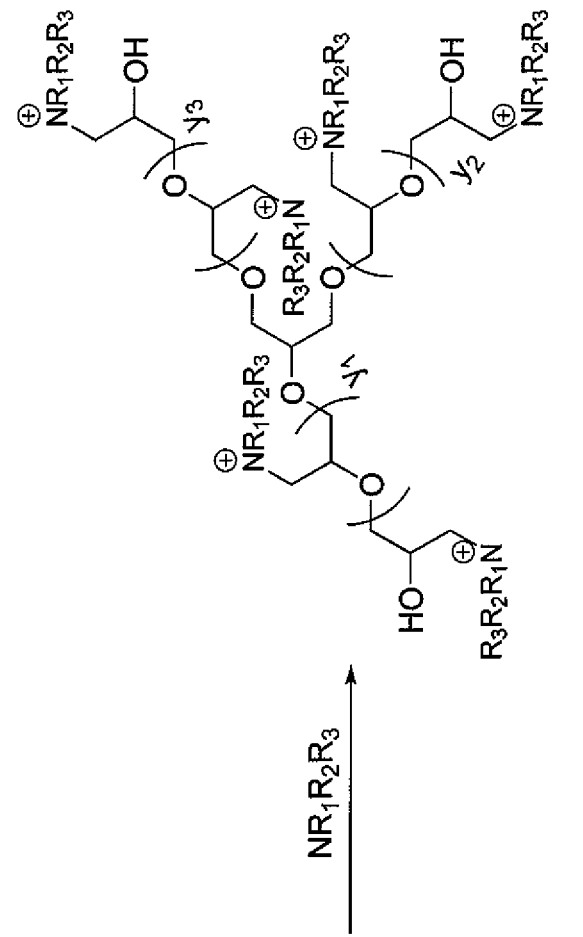
FIG. 2 illustrates the general structure of quaternized and branched polyepihalohydrin compounds of the invention.
Figure 2:
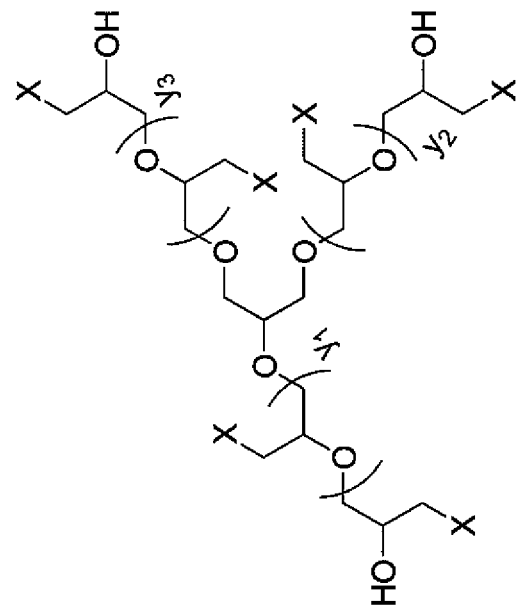

In an embodiment, the present invention relates to a reverse emulsion breaker composition comprising one or more polyepihalohydrins and a method of using the composition for resolving emulsions of water and oil. FIG. 1 illustrates the general structure of such polymers and FIG. 2 illustrates an embodiment where the polymers are quaternized and branched. In FIG. 1, X is a leaving group, such as chloride, bromide, iodide, trifluoromethylsulfonate, toluenesulfonate, methylsulfonate, the like, and combinations thereof. The leaving group is preferably chloride, bromide, iodide, or a combination thereof. The acid is a Lewis of Bronsted Acid, preferably $BF_3$ and/or ALMe3. y1, y2, and y3 independently range from about 2 to about 20. In a preferred embodiment, y1, y2, and y3 independently range from about 3 to about 15. In a more preferred embodiment, y1, y2, and y3 independently range from about 5 to about 10. Higher epihalohydrin to glycerol ratios, for example, lead to higher y values. For example, a 5:1 epi:alcohol (e.g., glycerol) ratio, y=2-3, for 10:1 ratio y=6-7, for 20:1 y=14-15, etc. In FIG. 2, X is a leaving group as described above. $R_1$, $R_2$, and $R_3$ are independently any alkyl or aryl group or hydrogen. Preferred are methyl and/or ethyl.

"Alkyl" refers means a monovalent group derived from a straight or branched chain saturated hydrocarbon by the removal of a single hydrogen atom. Representative alkyl groups include methyl, ethyl, n- and iso-propyl, cetyl, and the like. Preferred alkyls are methyl and ethyl.

"Aryl" refers an aromatic monocyclic or multicyclic ring system of about 6 to about 10 carbon atoms. The aryl is optionally substituted with one or more $C_1$-$C_{20}$ alkyl, alkoxy or haloalkyl groups. Representative aryl groups include phenyl or naphthyl, or substituted phenyl or substituted naphthyl.

In a further embodiment, the composition comprises at least one polyepihalohydrin, at least one polyelectrolyte thereof; and any combination thereof.

According to an embodiment, the disclosed reverse emulsion breakers may be used alone or in combination with any of a number of other emulsion breakers or demulsifiers known in the art. Typical demulsifiers for breaking crude oil emulsions that may have utility in the compositions herein are described, for example, in U.S. Pat. Nos. 2,470,829; 2,944,978; 3,576,740; 5,152,927; and 5,643,460. Other reverse emulsion breakers that may have utility in conjunction with the disclosed composition are disclosed in U.S. Pat. Nos. 5,032,085, "Reverse Emulsion Breaking Method Using Amine Containing Polymers" and 5,643,460, "Method for Separating Oil from Water in Petroleum Production."

In alternative embodiments, the disclosed composition for the reverse emulsion breaker generally depends upon the emulsion properties of the produced fluids. More specifically, the reverse emulsion breaker composition is formed from an effective amount of one or more polyepihalohydrins. The composition may contain any amount of the composition sufficient to produce a water clarification. The reverse emulsion breaker composition can be made in a variety of concentrations including between broadly trace to about 100% or about 1% to about 99% by weight of the composition or between about 10% and about 90% by weight of the composition. More specifically, the reverse emulsion breaker can be added in an amount equal to between about 20% and about 80% by weight of the composition or, about 40% and about 70% by weight of the reverse emulsion breaker composition. More preferably, the reverse emulsion breaker is added in an amount equal to between about 25% and about 50% by weight of the reverse emulsion breaker composition.

In an alternative embodiment, other solvents may be included with the polyepihalohydrin reverse emulsion breaker of the invention whereby the solvent can be added in an amount ranging between about 1% and about 10% by total weight of the formulation composition. Again, broadly, the reverse emulsion breaker composition can include an amount of the polyepihalohydrin ranging between trace or about 1% and up to about 99% or 100% by weight of the demulsifier composition. Typical solvents comprise water and/or low molecular weight alcohols.

The amount of the reverse emulsion breaker composition used depends on the particular water external emulsion being treated. In general, the effective amount of reverse emulsion breaker composition ranges from between about 1 ppm to about 5,000 ppm actives based on the total emulsion volume. More preferably, the dosage range is from about 1 ppm to about 1,000 ppm actives based on total emulsion volume. In another embodiment, the dosage is from about 10 ppm to about 1,000 ppm actives based on total emulsion volume.

Introducing the reverse emulsion breaker composition into the emulsion can be accomplished by any suitable method. For example, the composition may be injected into the crude oil at the well-head, or injected into the crude oil up-stream of the water separation vessels (such as free water knock-out or heat treater vessels). The reverse emulsion breaker may also be injected into the oil contaminated water upstream of the water floatation cells or upstream of skim tanks. The reverse emulsion breaker composition may be injected continuously or in batch fashion. The injection step is preferably accomplished using electric or gas pumps, but any suitable pumping device may be used.

The treated water external crude oil emulsion is then allowed to separate into distinct layers of water and oil. Once separation into distinct layers of water and oil has been effected, various means known in the art can be utilized for withdrawing the free water and separating crude oil. In a typical process for water clarification of produced water, a reservoir is provided to hold the composition of the invention in either diluted or undiluted form adjacent to the point of chemical injection. The role of the reverse emulsion breaker is usually to clean and oil free water for discharge. It should be appreciated that the invention has equal application for all processes in the petroleum industry.

Preferred polyepihalohydrins of the invention include polyepichlorohydrin, polyepibromohydrin, polyepiiodohydrin, the like, and combinations thereof. The molecular weight range of these polymers is generally from about 400 to about 20,000 Mn (number average molecular weight).

In synthesizing the polyepihalohydrins of the invention, a wide range of polyols with a Lewis acid catalyst may be used to initiate the reaction as well as the alkoxylated (e.g., ethoxylated or propoxylated) analogs thereof. Representative polyols include trimethylol propane, glycerol, polyglycerol, pentaerythritol, sorbitol, the like, and combinations thereof. In alternative embodiments, any polyol known in the art or equivalents may be used in to initiate the synthesis reaction. Representative Lewis acids include alkyl aluminum compounds (e.g., triisobutyl aluminium, triethyl aluminum, diisobutyl aluminum chloride, monoisobutyl aluminum chloride, and aluminum isoproylate), $BF_3$, $HPF_6$, and $SnCl_4$, the like, and combinations thereof. In alternative embodiments, any Lewis acid known in the art or equivalents may be used in the reaction sequence. Represenative Bronsted acids include but are not limited to HCl, $H_2SO_4$, HClO, HBr, or combinations thereof. In alternative embodiments, any Lewis or Bronsted acid known in the art or equivalents thereof may be used in the reaction sequence.

Figure 3:
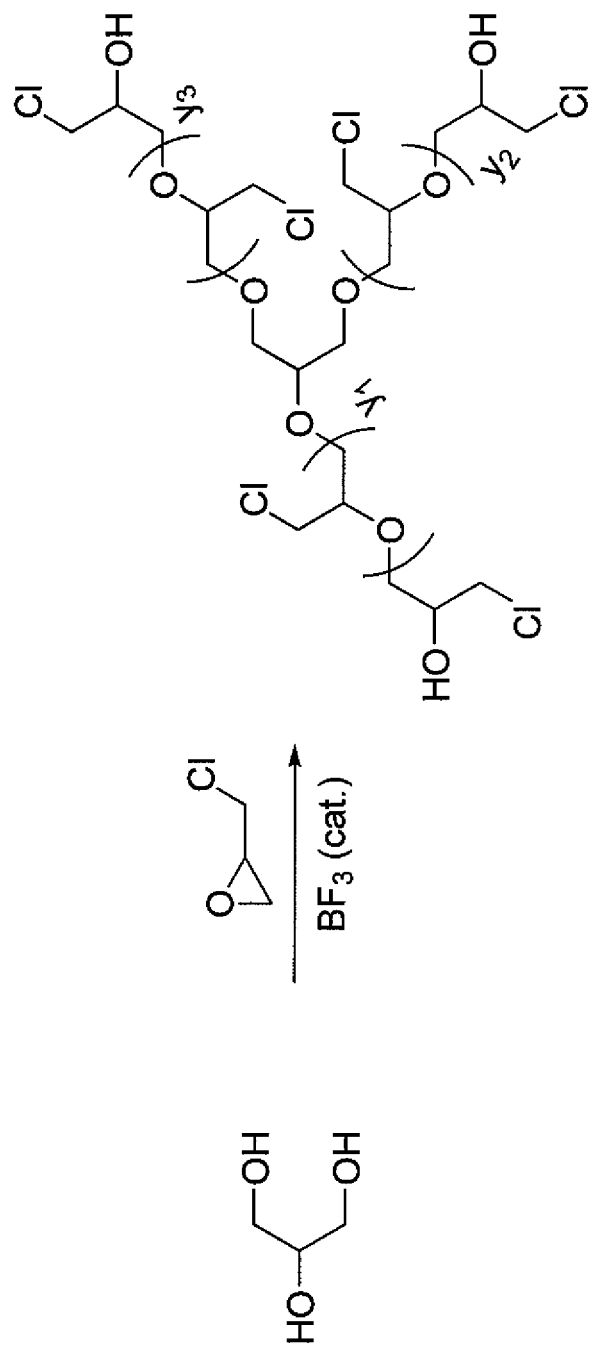
FIG. 3 illustrates an embodiment for synthesis of branched polyepichlorohydrin.

A preferred polyepichlorohydrin for use in the reverse emulsion breaker of the invention is a quaternized, branched polyepichlorohydrin. Referring to FIG. 3, polymerizing epichlorohydrin, in the presence of a polyol and a Lewis acid catalyst generates the preferred branched polyepichlorohydrin of the invention. The molecular weight of the polyepichlorohydrin is generally controlled by the ratio of epichlorohydrin to polyol in the reactant mixture. By varying this ratio from about 5:1 to about 20:1, it is possible to produce polymers with molecular weights ranging from about 400 to about 3,000 Mn.

Figure 4:
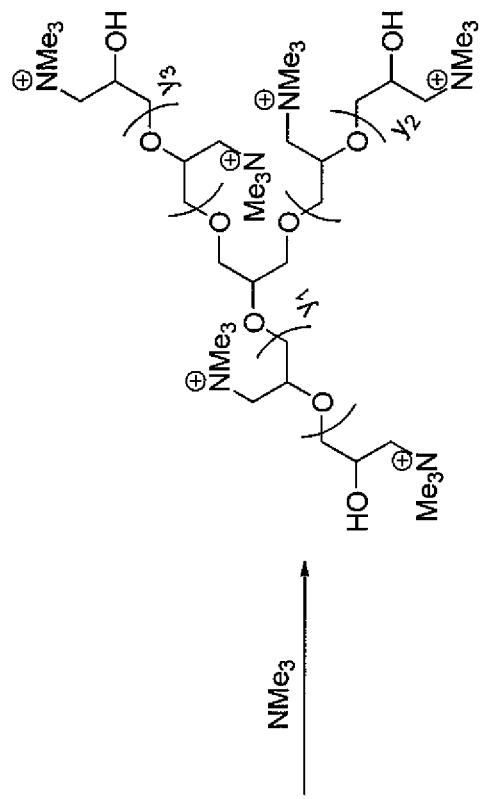
FIG. 4 illustrates an embodiment for the quaternization of branched polyepichlorohydrin.
Figure 4:
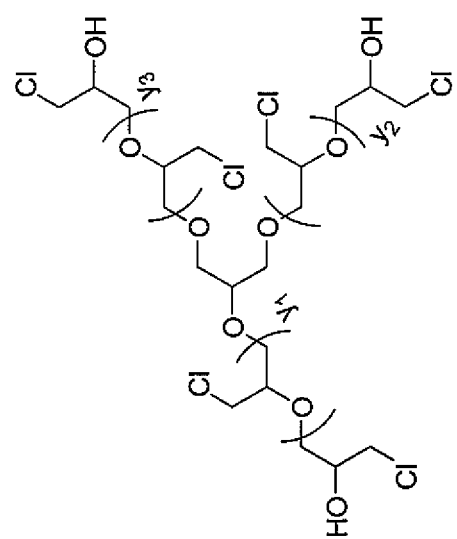

In a second reaction step upon obtaining the branched polyepichlorohydrin, a primary, secondary, and/or tertiary amine is used to yield the final polyelectrolyte, as shown in FIG. 4. Examples of these amines include ammonia, methylamine, trimethylamine, triethylamine, dimethylamine, diisopropylethylamine, piperadine, pyridine, the like, and combinations thereof. Additionally, polyamines may also be used in this step to generate crosslinking and higher molecular weight polyelectrolytes. Representative polyamines include ethylendiamine, diethylenetriamine, tetramethylethylenediamine, tetraethylenepentaamine, the like, and combinations thereof.

In an embodiment, at any time prior to functionalization the central core of the polyol has 3 or more accessible alcohol functional groups as in general formula (1) below.

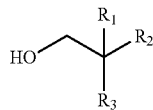

(1)

Where, $R_1$ and $R_2$ are selected from H, alkyl, OH, $CH_2OH$, $C_4H_9O_4$, sorbitol, other sugar alcohols, and the like. $R_3$ is selected from OH, $CH_2OH$, $C_4H_9O_4$, sorbitol, other sugar alcohols, polyclycerol, polyetheyleneoxide, polypropyleneoxide, and the like.

In an embodiment, the polyol is reacted as shown below, where $R_4$ is shown as general formula (2) below. X ranges from about 2 to about 20, preferably from about 3 to about 15, and more preferably from about 5 to about 10.

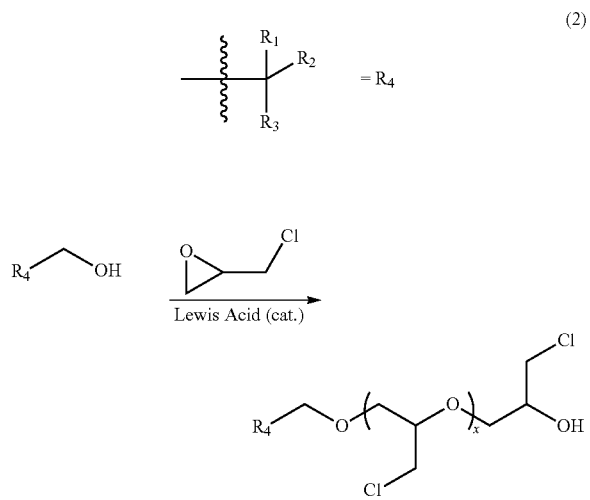

(2)

In an embodiment, a glycerol core is reacted where $R_4$ is shown as general formula (3) below. The product of this reaction is shown as general formula (4) below, where x, y, and z independently ranges from about 2 to about 20, preferably from about 3 to about 15, and more preferably from about 5 to about 10, again dependent on the epi to alcohol ratio.

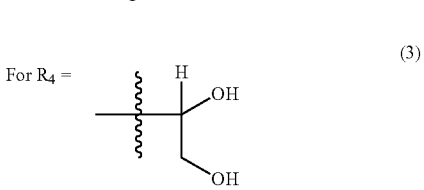

(3)

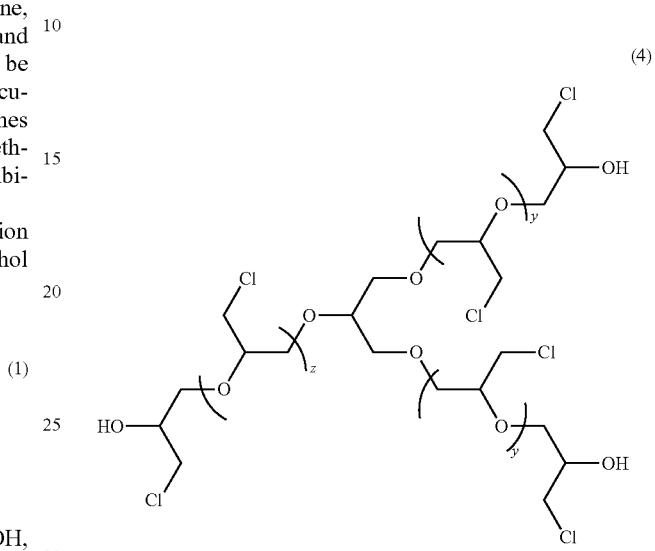

(4)

In embodiments, the reverse emulsion breaker composition of the invention is used to separate emulsions produced by alkali-surfactant-polymer or surfactant-polymer enhanced oil recovery floods. In such embodiments, the produced emulsions typically contain at least water, crude oil, surfactants, and polymers. Addition of the reverse emulsion breaker composition of the invention to the produced emulsion separates the oil and water phases. In some embodiments, the separation is a clean separation of oil and water. A clean separation generally refers to dry oil with less than about 1% total sediment and water, a good interface with sharp separation between oil and water, and clean water with less than about 300 parts per million (ppm) residual oil. The composition is added to the emulsion by any suitable method. For instance, examples of suitable methods include the methods disclosed in Z. Ruiquan et al., "Characterization and demulsification of produced liquid from weak base ASP flooding," Colloids and Surfaces, Vol. 290, pgs 164-171, (2006) and U.S. Pat. Nos. 4,374,734 and 4,444,654.

In another embodiment, the reverse emulsion breaker composition of the invention may have utility in stabilizing clays during fracturing of a subterranean reservoir. During the fracturing of subterranean reservoirs, clays native to the reservoir will often swell when brought into contact with injected water, lowering the efficiency of the fracturing process. Clay stabilizer products are mixed with the fracturing fluid (e.g., water) prior to injection to prevent clay swelling, thus enhancing the total efficiency of the fracturing process.

The foregoing may be better understood by reference to the following examples, which are intended for illustrative purposes and are not intended to limit the scope of the invention.

EXAMPLE 1

Reaction Scheme 1: To a 250 ml four-necked flask was added 16.8 g of trimethylolpropane. The flask was purged with $N_2$ and heated to 60° C. while stirring. One mL of $BF_3.OEt_2$ was then added and 231.3 g of epichlorohydrin was added dropwise over the course of an hour, maintaining the temperature between 85° C. and 95° C. Once the addition was completed, the resulting mixture was stirred at 95° C. for one hour. The temperature was then increased to 110° C. and the mixture mixtured was sparged with $N_2$ for one hour to yield the trimethylolpropane/epichlorohydrin copolymer.

Reaction Scheme 2: To a 250 ml four-necked flask was added 33.5 g of trimethylolpropane. The flask was purged with $N_2$ and heated to 60° C. while stirring. One mL of $BF_3.OEt_2$ was then added and 231.3 g of epichlorohydrin was added dropwise over the course of an hour, maintaining the temperature between 85° C. and 95° C. Once the addition was completed, the resulting mixture was stirred at 95° C. for one hour. The temperature was then increased to 110° C. and the mixture mixtured was sparged with $N_2$ for one hour to yield the trimethylolpropane/epichlorohydrin copolymer.

Reaction Scheme 3: To a 250 ml four-necked flask was added 92.1 g of glycerol. The flask was purged with $N_2$ and heated to 60° C. while stirring. One mL of $BF_3.OEt_2$ was then added and 231.3 g of epichlorohydrin was added dropwise over the course of an hour, maintaining the temperature between 85° C. and 95° C. Once the addition was completed, the resulting mixture was stirred at 95° C. for one hour. The temperature was then increased to 110° C. and the mixture mixtured was sparged with $N_2$ for one hour to yield the glycerol/epichlorohydrin copolymer.

Reaction Scheme 4: To a 500 mL hastelloy autoclave was added 50.3 g of trimethylolpropane/epichlorohydrin copolymer from Reaction Scheme 1. 66.5 g of a 45% aqueous solution of trimethylamine was then added to the autoclave and the autoclave was then sealed. The mixture was then heated to 100° C. and stirred at this temperature for 24 hours. After 24 hours, the autoclave was flushed with $N_2$ and cooled to room temperature to yield the trimethylamine quaternary salt of the trimethylolpropane/epichlorohydrin copolymer.

Reaction Scheme 5: To a 500 mL hastelloy autoclave was added 49.2 g of glycerol/epichlorohydrin copolymer from Reaction Scheme 1. 63.5 g of a 45% aqueous solution of trimethylamine (TMA) was then added to the autoclave and the autoclave was then sealed. The mixture was then heated to 100° C. and stirred at this temperature for 24 hours. After 24 hours, the autoclave was flushed with $N_2$ and cooled to room temperature to yield the trimethylamine quaternary salt of the glycerol/epichlorohydrin copolymer.

EXAMPLE 2

This example illustrates the effectiveness of the reverse emulsion breaker of the invention embodied in FIG. 4. It can be seen in Table 1 that the quaternized branched polyepichlorohydrin polyelectrolytes were found to yield cleaner water at lower treat rates than the traditionally used chemicals. Moreover, differences were observed between the branched and linear polyepichlorohydin (PECH) polyelectrolytes. Though both are effective reverse emulsion breakers and within the scope of the invention, the branched version has the advantage of being able to resolve the emulsion at a lower dose and provide cleaner water (Table 1, Samples 5 and 6) than there linear equivalents (Table 1, Samples 3, 4, 7, and 8). The branched molecules are also found to be less viscous than their linear counterparts making them easier to handle.

TABLE 1

| Sample | Chemical | Dose (ppm) | Reverse Emulsion (Resolved/Unresolved) | Turbidity (NTU) |
|---|---|---|---|---|
| 1 | MeCl quaternized polytriethanolamine | 160 | Unresolved | NA |
| 2 | polyDADMAC | 160 | Unresolved | NA |
| 3 | Linear low MW PECH.TMA quaternized. | 160 | Unresolved | NA |
| 4 | Linear high MW PECH.TMA quaternized | 160 | Unresolved | NA |
| 5 | Branched low MW PECH.TMA quaternized | 160 | Resolved | 363 |
| 6 | Branched high MW PECH.TMA quaternized | 160 | Resolved | 295 |
| 7 | Linear low MW PECH.TMA quaternized | 180 | Resolved | 455 |
| 8 | Linear high MW PECH.TMA quaternized | 180 | Resolved | 370 |

EXAMPLE 3

This example illustrates the effectiveness of the reverse emulsion breaker of the invention with regard to resolving reverse emulsions stabilized by anionic surfactant polymers. The reverse emulsion was generated by mixing 30 mL crude oil with 70 mL of an anionic surfactant solution in prescription bottles. The bottles were then place on a mechanical shaker for 10 minutes. The resulting mixture was then treated with the indicated chemical and shaken for an additional 3 minutes. The bottles were removed from the shaker and separation of the oil and water was monitored along with the resultant oil and water quality. It can be seen in Tables 2a and 2b that the branched polyepichlorohydrin quaternized molecules provided a faster water drop than linear counterparts as well as cleaner water.

Table 2a

| Sample | Chemical | Dose (ppm) | Water Drop (mL) | | | | | | Water Quality Turbidity (NTU) |
|---|---|---|---|---|---|---|---|---|---|
| | | | 1' | 5' | 10' | 40' | 1 h | 3 h | |
| 1 | Branched PECH.TMA quaternized | 450 | 18 | 63 | 65 | 68 | 70 | 70 | 552 |
| 2 | Linear PECH.TMA quaternized | 450 | 5 | 25 | 50 | 68 | 70 | 70 | 580 |
| 3 | Branched PECH.TMA quaternized | 600 | 60 | 68 | 68 | 68 | 70 | 70 | 404 |
| 4 | Linear PECH.TMA quaternized | 600 | 50 | 67 | 68 | 68 | 70 | 70 | 446 |
| 5 | Untreated | — | 0 | 10 | 12 | 40 | 50 | 60 | 857 |

9

Table 2b

| Sample | Chemical | Dose (ppm) | Total | % H$_2$O | % BS | Slug |
|---|---|---|---|---|---|---|
| 1 | Branched PECH.TMA quaternized | 450 | 0.4 | trace | 0.4 | 0.3 |
| 2 | Linear PECH.TMA quaternized | 450 | 0.4 | trace | 0.4 | 0.4 |
| 3 | Branched PECH.TMA quaternized | 600 | 0.4 | trace | 0.4 | 0.3 |
| 4 | Linear PECH.TMA quaternized | 600 | 0.4 | trace | 0.4 | 0.4 |
| 5 | Untreated | — | 10 | 0.8 | 9.2 | 10 |

EXAMPLE 4

This example illustrates the effectiveness of the invention as a clay stabilization agent. The effectiveness of the chemicals were measured via capillary suction timer (CST) testing by weighing 250 g deionized water into a 500 mL plastic beaker. The mixture was then stirred at a Variac reading of 40 using an overhead stirrer. The clay stabilizer candidate to be evaluated is added (0.25 mL; 1 gpt) to the water while stirring at this stage. A 30 g premixed clay (83/17 silica flour/sodium bentonite) was next added to the solution and stirred at 50 Variac for 1 min The stirring was stopped and the clay set aside for 5 min to allow time to hydrate. At the end of this interval the slurry is stirred at 40 Variac and 1cc portions of samples are withdrawn and syringed in through the sample port of the CST instrument. The CST value is read out from the display and recorded. Three such readings are taken consecutively and averaged out to report the CST value for the particular clay stabilizer additive at the studied dosage. In general, the lower the CST value the more effective the clay stabilization.

TABLE 3

| Sample | Chemistry | CST |
|---|---|---|
| 1 | Linear PECH.TMA quaternized | 35 |
| 2 | Branched PECH.TMA quaternized | 31 |
| 3 | Epichlorohydrin/dimethylamine copolymer | 42 |
| 4 | Methylchloride quaternized choline | 97 |
| 5 | Trimethylammonium chloride | 112 |

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method for resolving an emulsion of water and oil, the method comprising adding an effective amount of a reverse emulsion breaker composition to the emulsion of water and oil, the composition comprising at least one polyepihalohydrin having the following structure;

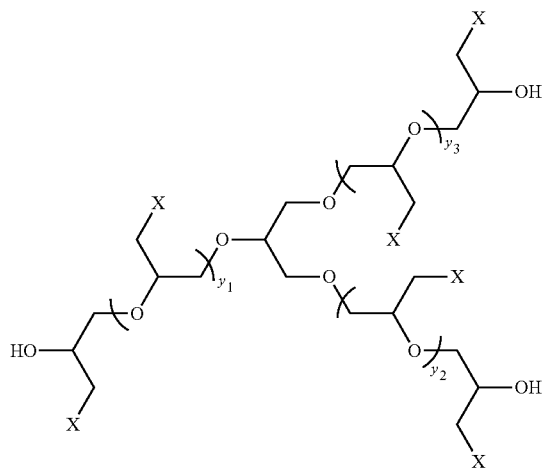

wherein, X is selected from chloride, bromide, iodide, trifluoromethylsulfonate, toluenesulfonate, methylsulfonate, and combinations thereof;
wherein y1 is from about 2 to about 20;
wherein y2 is from about 2 to about 20; and
wherein y3 is from about 2 to about 20.

2. The method of claim 1, wherein the emulsion is a simple water external emulsion of oil and water or a complex emulsion of oil and water.

3. The method of claim 1, wherein the at least one polyepihalohydrin is present in the composition from about trace to about 100 wt %.

4. The method of claim 1, wherein the composition further comprises at least one solvent.

5. The method of claim 1, wherein the oil is selected from the group consisting of: crude oil, refined oil, bitumen, condensate, slop oil, distillates, fuels, and mixtures thereof.

6. The method of claim 1, further comprising adding from about 1 ppm to about 5,000 ppm of said composition based on actives and total emulsion volume.

7. The method of claim 1, wherein the emulsion is a produced emulsion from an alkali-surfactant-polymer or surfactant-polymer enhanced oil recovery flood.

8. A method for resolving an emulsion of water and oil, the method comprising adding an effective amount of a reverse emulsion breaker composition to the emulsion of water and oil, the composition, comprising at least one polyepihalohydrin having the following structure:

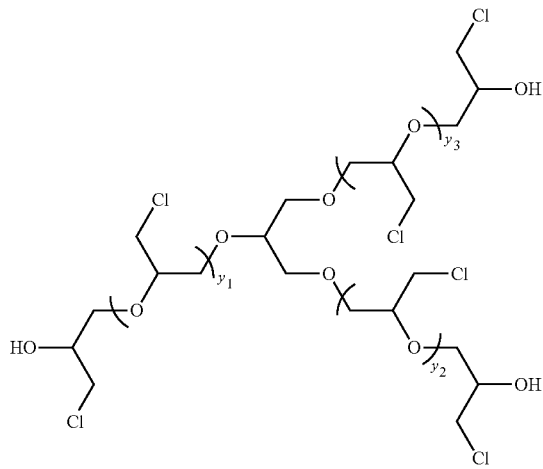

wherein y1 is from about 2 to about 20;

wherein y2 is from about 2 to about 20; and wherein y3 is from about 2 to about 20.

9. The method of claim 8, wherein the emulsion is a simple water external emulsion of oil and water or a complex emulsion of oil and water.

10. The method of claim 8, wherein the at least one polyepihalohydrin is present in the composition from about trace to about 100 wt %.

11. The method of claim 8, wherein the composition further comprises at least one solvent.

12. The method of claim 8, wherein the oil is selected from the group consisting of: crude oil, refined oil, bitumen, condensate, slop oil, distillates, fuels, and mixtures thereof.

13. The method of claim 8, further comprising adding from about 1 ppm to about 5,000 ppm of said composition based on actives and total emulsion volume.

14. The method of claim 8, wherein the emulsion is a produced emulsion from an alkali-surfactant-polymer or surfactant-polymer enhanced oil recovery flood.

15. A method for resolving an emulsion of water and oil, the method comprising adding an effective amount of a reverse emulsion breaker composition to the emulsion of water and oil, the composition, comprising at least one polyepihalohydrin having the following structure:

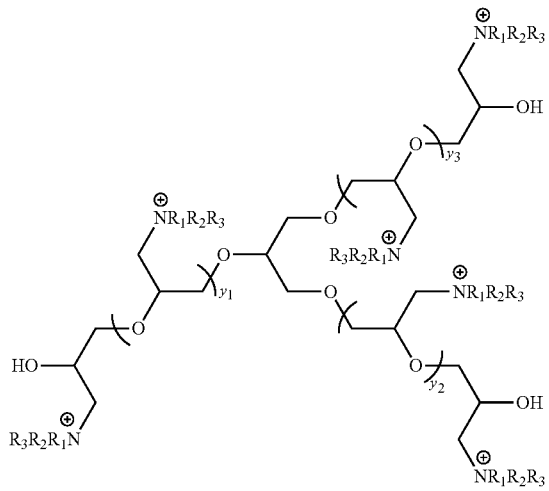

wherein $R_1$ is selected from alkyl or aryl or hydrogen;
wherein $R_2$ is selected from alkyl or aryl or hydrogen;
wherein $R_3$ is selected from alkyl or aryl or hydrogen;
wherein y1 is from about 2 to about 20;
wherein y2 is from about 2 to about 20; and
wherein y3 is from about 2 to about 20, wherein the emulsion is a produced emulsion from an alkali-surfactant-polymer or surfactant-polymer enhanced oil recovery flood.

16. A method for resolving an emulsion of water and oil, the method comprising adding an effective amount of a reverse emulsion breaker composition to the emulsion of water and oil, the composition comprising at least one polyepihalohydrin having the following structure:

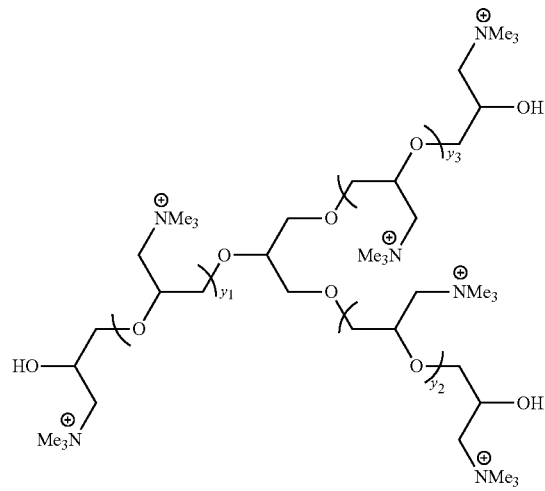

wherein y1 is from about 2 to about 20;
wherein y2 is from about 2 to about 20; and
wherein y3 is from about 2 to about 20, wherein the emulsion is a produced emulsion from an alkali-surfactant-polymer or surfactant-polymer enhanced oil recovery flood.

* * * * *